United States Patent [19]

Lin et al.

[11] Patent Number: 4,855,055
[45] Date of Patent: Aug. 8, 1989

[54] ISOLATION AND PURIFICATION OF PRE-S2 CONTAINING HEPATITIS B VIRUS SURFACE ANTIGEN BY CHEMICAL AFFINITY CHROMATOGRAPHY

[75] Inventors: J. Y. Lin; Yih-Shou Hsieh; Shu-Chen Chu, all of Taipei, Taiwan

[73] Assignee: National Science Council, Taipei, Taiwan

[21] Appl. No.: 250,062

[22] Filed: Sep. 28, 1988

[51] Int. Cl.$^4$ .................... B01D 15/08; A61K 39/12
[52] U.S. Cl. ............................ 210/635; 210/656; 424/89; 530/395; 530/413
[58] Field of Search ............... 424/89; 530/395, 413; 210/635, 656

[56] References Cited

U.S. PATENT DOCUMENTS

| | | | |
|---|---|---|---|
| 4,639,371 | 1/1987 | Prince | 424/89 |
| 4,683,136 | 7/1987 | Milich | 424/89 |
| 4,722,840 | 2/1988 | Valenzuela | 435/68 |
| 4,742,158 | 5/1988 | Lehman | 530/371 |

OTHER PUBLICATIONS

Dean, P. D. G. et al.–Affinity Chromatography, A Practical Approach, pp. 31–32, IRL Press, Oxford, England, 1985.
Neurath, A. R. et al.–Location and Chemical Synthesis of a Pre-S Gene Coded Immunodominant Epitope of Heptatitis B Virus, Science, vol. 224, pp. 392–395, Apr. 27, 1984.
Neurath, A. R. et al.–Hepatitis B. Virus Contains Pre-S Gene-Encoded Domains, Nature, vol. 315, pp. 154–156, May 9, 1985.
Lenkei, R. et al.–Correlations Between Anti-Albumin Antibodies and HB$_s$AG in Hepatic Patients, Journal of Medical Virology 1, pp. 29–34, 1977.
Machida, A. et al.–A Hepatitis B Surface Antigen Polypeptide (P31) With the Receptor for Polymerized Human as Well as Chimpanzee Albumins, Gastroneterology, vol. 85, No. 2, pp. 268–274, 1983.
Stibbe, W. et al.–Structural Relationships Between Minor and Major Proteins of Hepatitis B Surface Antigen, Journal of Virology, vol. 46, No. 2, pp. 626–628, May 1983.
Hansson et al.–Sites that Bind Polymerized Albumin on Hepatitis B Surface Antigen Particles: Detection by Radioimmunoassay, Infection and Immunity, vol. 26, No. 1, pp. 125–130, Oct. 1979.
Towbin et al.–Electrophoretic Transfer of Proteins from Polyacrylamide Gels to Nitrocellulose Sheets: Procedure and Some Applications, Proc. Nat. Acad. Sci., vol. 76, No. 9, pp. 4350–4354, Sep. 1979.
Heermann et al.–Large Surface Proteins of Hepatitis B Virus Containing the Pre-S Sequence, Journal of Virology, vol. 52, pp. 396–402, Nov. 1984.
Michel, M. L. et al.–Expression of Amplified Hepatitis B Virus Surface Antigen Genes in Chinese Hamster Ovary Cells, Biotechnology, vol. 3, pp. 561–567, Jun. 1985.
Yu, M. W. et al.–Interaction Between Various Polymerized Human Albumins and Hepatitis B Surface Antigen, Journal of Virology, vol. 55, pp. 736–743, Sep. 1985.
Laemmli, U. K.–Cleavage of Structural Proteins During the Assembly of the Head of Bacteriophage T4, Nature, vol. 227, pp. 680–685, Aug. 15, 1970.
Prince, A. M. et al.–Comparative Evaluations of Hepatitis B Vaccines in Chimpanzees and in Man, pp. 507–523.
Fujisawa, Y. et al.–Expression of Hepatitis B Virus Surface Antigen P31 Gene in *Escherichia Coli*, Elesvier Science, pp. 23–29, 1985.
Interaction of Hepatitis B Surface Antigen With Polymerized Human Serum Albumin, Journal of Medical Virology, vol. 4, pp. 177–185 (1979).
Hepatitis B Virus Infection, The Western Journal of Medicine, pp. 754–762, May 1984.

*Primary Examiner*—Ernest G. Therkorn
*Attorney, Agent, or Firm*—Cushman, Darby & Cushman

[57] ABSTRACT

A method for isolating and purifying pre-S2 containing HBsAg from the plasma of a carrier of HBsAg characterized by the use of polymerized human serum albumin (pHSA)-affinity column chromatography.

9 Claims, 3 Drawing Sheets

ISOLATION AND PURIFICATION OF PRE-S2 CONTAINING HEPATITIS B VIRUS SURFACE ANTIGEN BY CHEMICAL AFFINITY CHROMATOGRAPHY

FIELD OF THE INVENTION

The invention relates to a method for isolating and purifying pre-S2 containing hepatitis B virus surface antigen (HBsAg) from the plasma of a carrier of HBsAg characterized by the use of polymerized human serum albumin (pHSA)-affinity column chromatography, comprising the steps of ammonium sulfate fractionation, hydroxyapatite column chromatography and pHSA-affinity column chromatography.

BACKGROUND OF THE INVENTION

Chinese people are suffering the highest incidence of hepatocellular carcinoma among the world population. Hepatitis B virus (HBV) causes the acute and chronic hepatitis, and is most likely an important agent to cause hepatocellular carcinoma (Vyas, G. N. et al., Western J. Med. 140:754-762, 1984). HBV envelope contains hepatitis B virus surface antigen (HBsAg) carried with the major polypeptides with a molecular weight 26,000, its glycosylated derivative with a molecular weight of 30,000, and two minor polypeptides with the a molecular weight of 31,000 and 68,000, respectively. The minor polypeptides are carrying the receptor activity for polymerized human serum albumin (pHSA) (Machida, A. et al., Gastroenterology 85:268-274, 1983; Stibbe, W. et al., J. Virol. 46:626-628, 1983; Hansson, B. G. et al., Infect. Immun. 26:125-130, 1979; O'Neill, S. P., J. Med. Virol. 4:177-185. 1979; Towbin, H. et al., Proc. Natl. Acad. Sci. USA 76:4350-4354, 1979).

The purification of HBsAg was reported previously by several other research institutes, and the methods they employed are similar but not identical (Michida, A. et al., supra; Michel, M-L. et al., Biotechnology 3:561-566, 1985; Heermann, K. H. et al., J. of Virol. 52:396-402, 1984). The common principle they used for purification of HBsAg is to apply a series of rate zonal centrifugation, first by sucrose density gradient centrifugation, followed by CsCl density gradient centrifugation. However, by those methods, pre-S containing HBsAgs are purified together with HBsAgs without pre-S peptide.

The present invention develops a simple method for fast and efficiently isolating and purifying pre-S2 containing HBsAgs from the plasma of a single chronic carrier of HBsAg (adw) by ammonium sulfate fractionation, hydroxyapatite column chromatography and pHSA affinity column chromatography. About 500 μg of pre-S2 containing HBsAg was obtained from 140 ml of plasma containing 4,200 μg of HBsAg. Two purified pre-S2 containing HBsAgs were analyzed by SDS-polyacrylamide gel electrophoresis and their molecular weights were determined to be 31,000 and 68,000 respectively.

The present invention revealed that pHSA bound pre-S2 containing HBsAg specifically, and no significant amount of HBsAg (MW 26,000) or its glycosylated derivative (MW 30,000) was adsorbed by pHSA. These results are in an agreement with those of Yu, M. W. et al., (J. Virol. 55:736-743, 1985) or Machida, A. et al supra, and they showed that HBsAg particles were also bound by pHSA, probably due to the presence of pre-S HBsAg in the particles.

Since pHSA binds to pre-S2 containing HBsAg but it does not bind to HBsAg without pre-S, it strongly suggests that pre-S2 region has the binding site for pHSA. Neurath, A. R. et al (Science 224:392:395, 1985) reported that the 55 amino acid residues of pre-S2 region contained the epitopes for immunoglobulin of hepatitis B virus and that the synthetic peptide of the first 26 amino acid terminal residues was shown to induce antibodies. The pre-S2 structure was suggested to be involved in the attachment of HBV to liver cells. Therefore, to induce the antibodies against the infection by HBV, the pre-S2 containing HBsAg could be a much better antigen than HBsAg for preparing the vaccine against hepatitis B virus infection.

The present invention can be applied for the recovery of pre-S2 containing HBsAg produced by recombinant DNA techniques such as the expression of pre-S2 containing HBsAg in *Escherichia coli* (Fujisawa, Y. et al., Gene 40:23-29, 1985) or Chinese hamster ovary cells (Michel, M-L. et al., supra).

In the present invention, the pHSA-Sepharose 4B affinity column chromatography technique was employed as a major and important step for the purification of pre-S2 containing HBsAg. By using pHSA-Sepharose 4B affinity chromatography, it has the following advantages: (1) it is simple, fast and efficient as described above, (2) it has the specific affinity towards pre-S2 containing HBsAg, and (3) it is superior to immunoadsorbant affinity chromatography, because pHSA is the product made from normal human serum, while for immunoadsorbant affinity technique, the materials are obtained from monoclonal antibody of hybridoma or polyclonal antibody of immuned human being, which are suffered either from the safety or economic problems.

SUMMARY OF THE INVENTION

A simple, rapid and efficient method was developed to isolate and purify pre-S2 containing HBsAgs from the plasma of a single chronic carrier of HBsAg (adw) by ammonium sulfate fractionation, hydroxyapatite column chromatography and pHSA affinity column chromatography. The pHSA-Sepharose 4B affinity column chromatography technique was employed as the major and important step for the purification of pre-S2 containing HBsAg.

Two purified pre-S2 containing HBsAgs were analyzed by SDS-polyacrylamide gel electrophoresis and their molecular weights were determined to be 31,000 and 68,000 respectively. Since pHSA binds to pre-S2 containing HBsAg but it does not bind to HBsAg without pre-S, no significant amount of HBsAg or its derivative was detected in the final product.

About 500 μg of pre-S2 containing HBsAg was obtained from 140 ml of plasma containing 4,200 μg of HBsAg. The purity of the final purified pre-S2 containing HBsAg was examined quantitatively with a densitometer. On the basis of pre-S2 containing HBsAg polypeptides, the purity was estimated to be 92%. An overall yield, 8.8% of total HBsAg activity is obtained, which was based on commercial RIA kits from Abbott Laboratories.

These features and advantages of the present invention will become apparent from the following description, which, when taken in conjunction with the accompanying drawings, discloses presently preferred em-

DESCRIPTION OF THE PREFERRED EMBODIMENT

Figure 1:
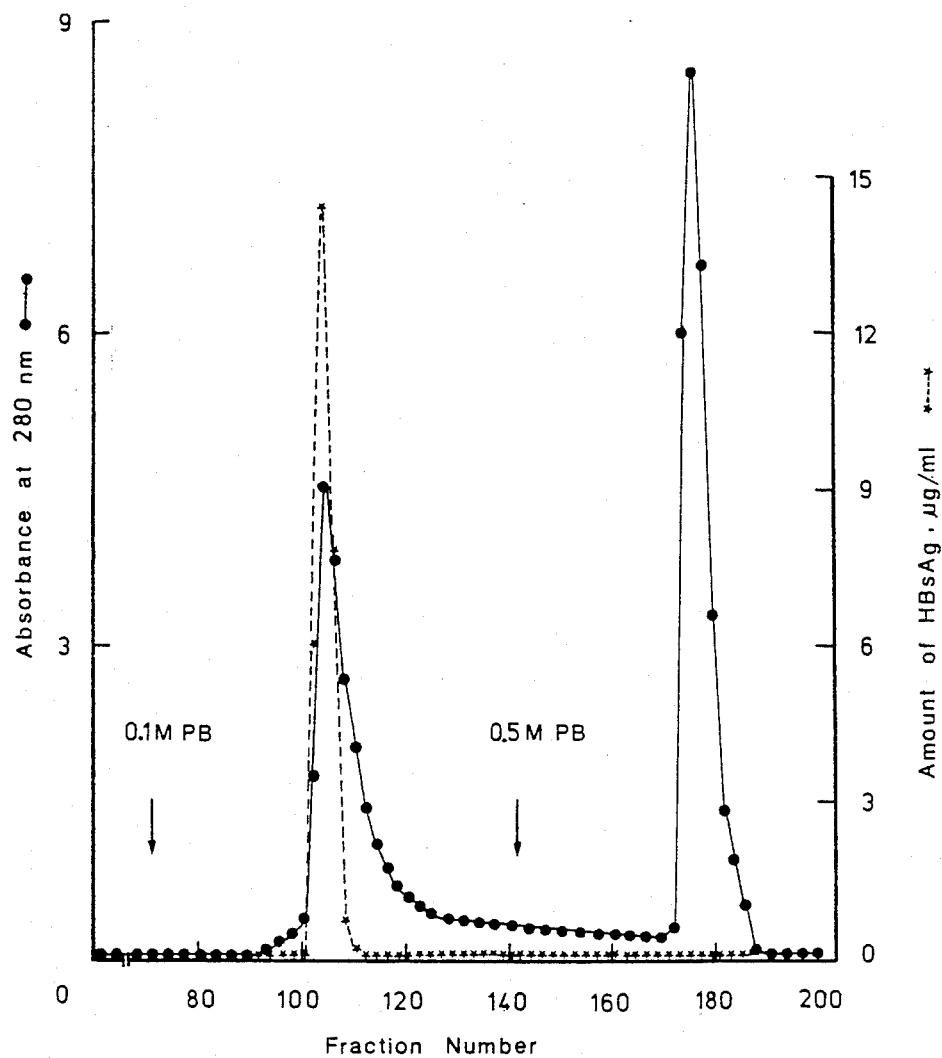
FIG. 1 shows the fractionation of pre-S2 containing HBsAg and HBsAg by column chromatography with a hydroxyapatite column (2.2×40 cm). The column was first eluted with 0.1M phosphate buffer pH 6.8, and then with 0.5M phosphate buffer pH 6.8. Pre-S2 containing HBsAg and HBsAg were found in the first peak. The flow rate was 30 ml/hour, and each fraction of 4 ml was collected.

The present invention is directed to a method for isolating and purifying pre-S2 containing HBsAgs from the plasma of a carrier of HBsAG characterized by the use of pHSA-affinity column chromatography.

Particularly, the present invention is directed to a method for isolating and purifying pre-S2 containing HBsAgs from the plasma of a carrier of HBsAg comprising the successive steps of ammonium sulfate fractionation, hydroxyapatite column chromatography and pHSA-affinity column chromatography.

In one embodiment, the present invention is directed to a method for isolating and purifying pre-S2 containing HBsAgs from the plasma of a carrier of HBsAg comprising the steps of:

(1) treating the plasma by heating, and centrifuging to collect the clear supernatant;

(2) then effecting ammonium sulfate fractionation, centrifuging to collect the precipitates and then dialyzing the precipitates against phosphate buffer;

(3) applying the dialyzate from (2) to a hydroxyapatite column;

(4) subjecting the fractions eluted from said hydroxyapatite column to step (2);

(5) applying the dialyzate from (4) to a pHSA-affinity column;

(6) neutralizing the fractions eluted from said pHSA-affinity column immediately with NaOH.

MATERIALS AND METHODS

Human serum albumin and glutaraldehyde (99% purity) were purchased from Sigma Chemical Company. Sepharose 4B was the product of Pharmacia Co. Hydroxyapatite was purchased from Bio-Rad Laboratories.

Preparation of Polymerized Human Serum Albumin (pHSA)

The preparation of pHSA was carried out according to the method of Lenkei, R. et al., (J. Med. Virol. 1:29-34, 1977). Human serum albumin 200 mg was dissolved in 9 ml of 0.1M phosphate buffer pH 6.8 and 1 ml of 2.5% glutaraldehyde was added. The reaction mixture was kept at room temperature for 2 hrs and then at 4° C. for 12 hrs, and the reaction was terminated by dialyzing against 0.01M phosphate buffered saline (PBS) pH 6.8 at 4° C. for 36 hrs. The dialyzate was further purified by gel filtration using a Sepharose 4B column (1.6×90 cm) to remove monomeric and dimeric albumins. The flow rate was 15 ml/hour, and each fraction of 4 ml was collected. The fractions containing the polymerized albumin were pooled, concentrated and dialyzed against PBS, pH 7.0 at 4° C. for 36 hrs. This preparation was designated as pHSA.

pHSA prepared by the present method was found by gel filtration to contain 1% of monomeric and 2% dimeric forms respectively. The fractions of polymers were pooled for the purpose of purification of pre S2-HBsAg.

Preparation of pHSA-Sepharose 4B (pHSA-S-4B) Affinity Column

Sepharose 4B gel was first activated with cyanogen bromide (CNBr) according to the method described by Dean P. D. G., et al, (Affinity Chromatography, a practical approach. p. 32. IRL Press. Oxford, England, 1985), 70 gm gel was treated with 1.6 g of CNBr at pH 11.0 for 20 min. The CNBr activated gel was washed with 0.1M sodium bicarbonate buffer pH 9.0 and then it was coupled with pHSA in 0.05M borate buffer pH 10.5 at 4° C. for 12 hrs. In order to react all the activated Sepharose hydroxy groups, the unreacted groups were blocked by reacting the gel with 0.1M glycine in 0.05M borate buffer, pH 10.5 for 6 hrs at 4° C.

Purification of Pre-S2 Containing HBsAg

All pre-S2 containing HBsAgs purified in the present invention were obtained from a single chronic carrier of HBsAg (adw).

The plasma was treated with 60° C. for 10 hours and centrifuged at 10,000×g for 30 min to remove the insoluble particles present in the plasma. The clear supernatant was subjected to ammonium sulfate fractionation; HBsAgs were precipitated between 15 and 45% saturation of ammonium sulfate. The precipitates were collected by centrifugation at 10,000×g for 20 min. The precipitates were dissolved in a minimum volume of water, and then dialyzed against 0.01M potassium phosphate buffer, pH 6.8. The dialyzate was applied to a hydroxyapatite column (2.2×40 cm) which was previously equilibrated with 0.01M potassium phosphate buffer pH 6.8. The column was first eluted with 0.1M equilibrium buffer, and then with 0.5M the same buffer. The flow rate was 30 ml/hour, and each fraction of 4 ml was collected. As shown in FIG. 1, Pre-S2 containing HBsAg and HBsAg detected in the first peak were eluted with 0.1M phosphate buffer, pH 6.8, while the second peak eluted by 0.5M phosphate buffer was found to be contaminating proteins.

The fractions containing HBsAg were pooled and concentrated by ammonium sulfate as described above.

The dialyzate was then fractionated by affinity chromatography using a pHSA-Sepharose 4B affinity column. The column (0.9×35 cm) was preequilibrated with 0.01M PBS, pH 6.8. After the application of the dialyzate to the column, the column was first eluted with equilibrium buffer and then eluted with 0.01 N HCl. The flow rate was 12 ml/hr, and each fraction of 2 ml was collected. The fractions eluted with 0.01N HCl were neutralized immediately with 0.01 N NaOH and subjected to quantitative analysis with RIA kits and qualitative analysis by SDS-PAGE.

Figure 2:
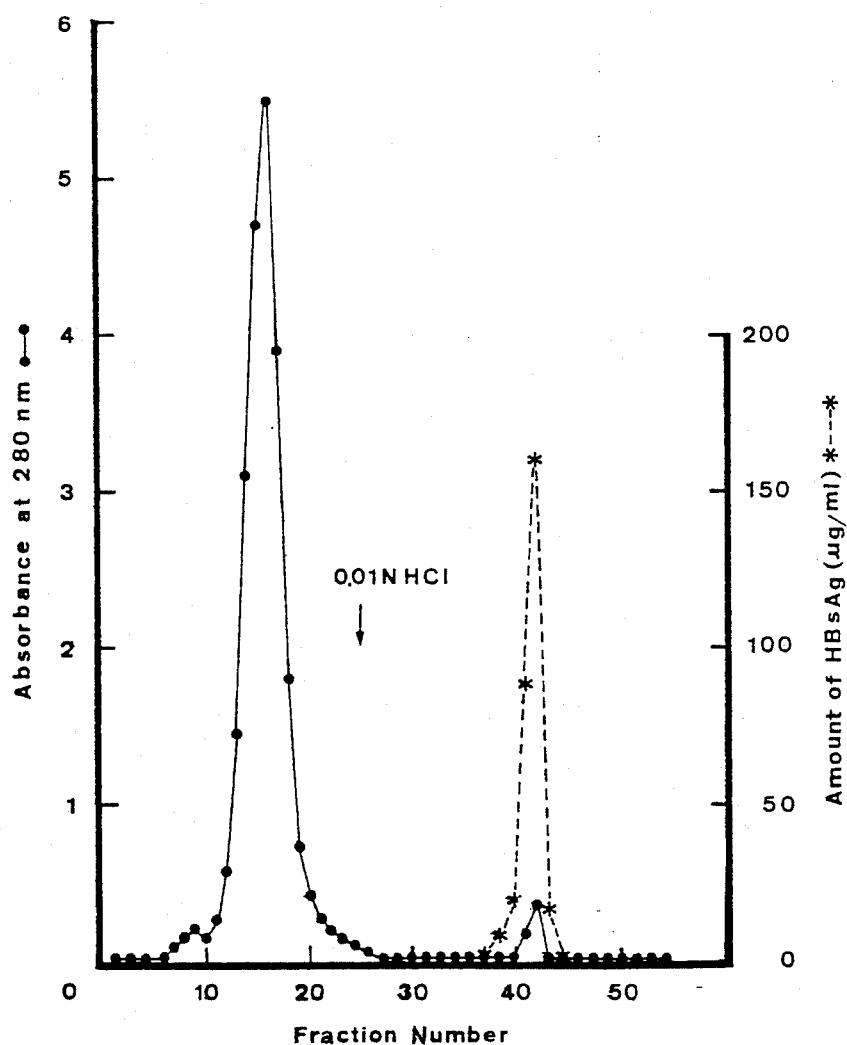
FIG. 2 shows the purification of pre-S2 containing HBsAg by glutaraldehyde polymerized human serum albumin affinity column chromatography. The column (0.9×35 cm) was first eluted with 0.01M phosphate buffered saline, pH 6.8, and then pre-S2 containing HBsAg was eluted with 0.01M HCl. The flow rate was 12 ml/hour and each fraction of 2 ml was collected.

The results were summarized in FIG. 2. The first peak was eluted with 0.01M phosphate buffered saline, pH 6.8 and was found to be HBsAg without pre-S2 as well as other contaminating proteins. The second peak was eluted with 0.01 N HCl, and was found to contain two pre-S2 containing HBsAgs as shown by SDS polyacryamide gel electrophoresis. The acidity of second peak was neutrlized with 0.1N NaOH right after elution from the column. The yield of pre-S2 containing HBsAg of a typical experiment is about 500 μg from 140 ml plasma of starting material which contained about 4,200 μg surface antigens.

The results of one of the typical experiments used to isolate and purify pre-S2 containing HBsAg are summarized in Table I. An overall yield, 8.8% of total HBsAg activity is obtained, which was based on commercial RIA kits from Abbott Laboratories.

TABLE 1

Purification of pre-S containing HBsAg

| Step | | Volume | Titer | Total activity | $A_{280}$ | Total $A_{280}$ | Yield (%) |
|---|---|---|---|---|---|---|---|
| 1. | HBeAg+ plasma | 140 ml | 30.0 μg/ml | 4200 μg | 60.4 | 8456 | 100 |
| 2. | 60° C., 10 hrs | 185 ml | 12.0 μg/ml | 2220 μg | 9.3 | 1721 | 52 |
| 3. | Ammonium sulfate | 43 ml | 48.8 μg/ml | 2098 μg | 25.4 | 1092 | 50 |
| 4. | Hydroxyapatite | 250 ml | 8.1 μg/ml | 2525 μg | 1.7 | 425 | 48 |
| 5. | pHSA-Sepharose 4B | 10 ml | 50.0 μg/ml | 500 μg | 0.06 | 0.6 | 8.8 |

Determination of HBsAg

HBsAg was quantitatively determined by using commercial radioimmunoassay (RIA) kits from Abbott Laboratories. It was carried out by using a standard from NIH in a parallel line assay (Prince, A. M., Vnek, J., Brotman, B., Harshmoto, N. and van der Endie, M. C. (1978), Comparative evaluations of hepatitis B vaccines in chimpanzees and in man, p.507–523. In Vyas, G. N. Cohen, S. N. and Schmid, R. (eds.), Viral hepatitis:etiology, epidemiology, pathogenesis and prevention. Franklin Inst. Press. Philadelphia).

Sodium Dodecyl Sulfate-Polyacrylamide Gel Electrophoresis (SDS-PAGE)

The pre-S2 containing HBsAg isolated and purified by pHSA-Sepharose 4B column chromatography was subjected to SDS-polyacryamide gel electrophoresis analysis.

Figure 3A:
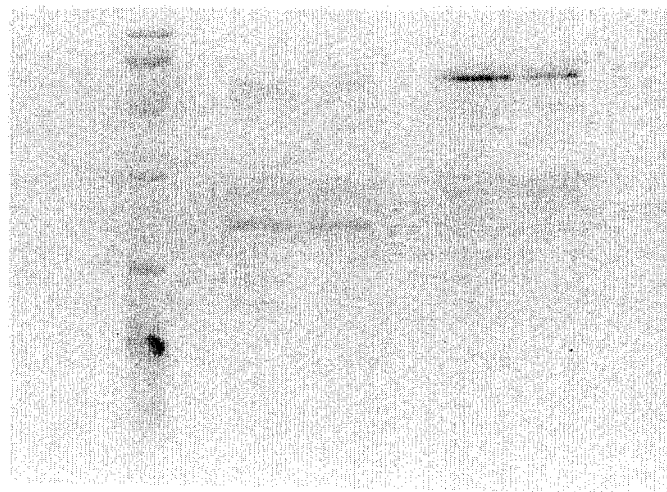
FIG. 3(A) shows the SDS-polyacrylamide gel electrophoresis of pre-S2 containing HBsAg detected by Silver staining method. Lane 1 shows standard protein bands, from top to bottom: phosphorylase b, albumin, ovalbumin, carbonic anhydrase, trypsin inhibitor, alpha-lactalbumin. Lanes 2 & 3 show CsCl density gradient centrifugation purified HBsAg which was treated with 5% MSH and 8M urea. Lanes 4 & 5 show purified pre-S2-HBsAg which was treated with 5% MSH and 8M urea.
Figure 3B:
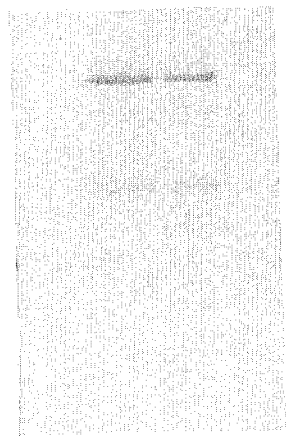
FIG. 3(B) shows the SDS-polyacrylamide gel electrophoresis of pre-S2 containing HBsAg detected by Western blotting method.

SDS-PAGE of slab gel was carried out according to the method of Laemmli, U.K. (Nature (London) 227:680–685, 1970). Purified HBsAg was treated with 1% SDS, 5% 2-mercaptoethanol and 8M urea in 0.0625M Tris-chloride buffer, pH 7.2 for 30 min at 100° C. to dissociate HBsAg polypeptides before electrophoresis. After electrophoresis, the gel was stained for protein by staining with 0.05% coomassie brilliant blue or 0.012M silver nitrate. The results were summarized in FIG. 3. Two pre-S2 containing HBsAgs were detected by silver stain as well as Western blot methods (Towbin, H. et al., supra). The apparent molecular weights of pre-S2 containing HBsAgs were measured to be 31,000 and 68,000, respectively.

For quantitation of pre-S2 containing HBsAgs, the gel which was stained for protein analysis, was scanned at a wavelength of 550 nm with an Auto Ciba Corning 780 Fluorometer/Densitometer (Ciba Corning Diagnostics Co. Medfield, Mass.). On the basis of pre-S2 containing HBsAg polypeptides, the purity was estimated to be 92%.

While the invention has been described in conjunction with specific embodiment, it is evident that numerous alternatives, modifications, and variations will be apparent to those skilled in the art in light of the foregoing description.

We claim:

1. A method for isolating and purifying pre-S2 containing HBsAgs from the plasma of a carrier of HBsAg comprising the sucessive steps of
   (1) treating the plasma by heating, and centrifuging to collect clear supernatant;
   (2) then effecting ammonium sulfate fractionation, centrifuging to collect precipitates and then dialyzing the precipitates against phosphate buffer;
   (3) applying the dialyzate from (2) to a hydroxyapatite column;
   (4) subjecting the fractions eluted from said hydroxyapatite column to step (2);
   (5) applying the dialyzate from (4) to a pHSA-affinity column; and
   (6) neutralizing the fractions eluted from said pHSA-affinity column immediately with NaOH.

2. A method according to claim 1, wherein said affinity column chromatography uses a pHSA-Sepharose 4B affinity column.

3. A method according to claim 2, wherein said affinity column is pre-equilibrated with 0.01M phosphate buffered saline, pH 6.8.

4. A method according to claim 3, wherein said affinity column is first eluted with 0.01M phosphate buffered saline, pH 6.8, and then with 0.01 N HCl, to obtain pre-S2 containing HBsAgs, the flow rate therof being 12 ml/hour.

5. A method according to claim 4, wherein the molecular weights of said pre-S2 containing HBsAgs are 31,000 and 68,000.

6. A method according to claim 1, wherein said plasma is treated at 60° C. for 10 hours.

7. A method according to claim 1, wherein pre-S2 containing HBsAgs are precipitated between 15 and 45% saturation of ammonium sulfate in the step of ammonium sulfate fractionation.

8. A method according to claim 1, wherein said hydroxyapatite column is previously equilibrated with 0.01M potassium phosphate buffer, pH 6.8.

9. A method according to claim 8, wherein said hydroxyapatite column is eluted with 0.1M phosphate buffer, pH 6.8, to obtain pre-S2 containing HBsAgs and HBsAg, the flow rate thereof being 30 ml/hour.

* * * * *